(12) United States Patent
Stancl

(10) Patent No.: US 10,450,267 B2
(45) Date of Patent: Oct. 22, 2019

(54) METHOD FOR PREPARING N-[4-(2-{[2-(4-METHANE SULFONAMIDOPHENOXY) ETHYL](METHYL)AMINO}ETHYL)PHENYL] METHANESULFONAMIDE (DOFETILIDE)

(71) Applicant: Farmak, A.S., Olomouc (CZ)

(72) Inventor: Marek Stancl, Brno (CZ)

(73) Assignee: Farmak, A.S., Olomouc (CZ)

( * ) Notice: Subject to any disclaimer, the term of this patent is extended or adjusted under 35 U.S.C. 154(b) by 0 days.

(21) Appl. No.: 16/204,413

(22) Filed: Nov. 29, 2018

(65) Prior Publication Data

US 2019/0169121 A1   Jun. 6, 2019

(30) Foreign Application Priority Data

Dec. 1, 2017   (CZ) .................................... 2017-772

(51) Int. Cl.
  *C07C 311/08* (2006.01)
  *C07C 303/36* (2006.01)
(52) U.S. Cl.
  CPC .......... *C07C 311/08* (2013.01); *C07C 303/36* (2013.01)
(58) Field of Classification Search
  None
  See application file for complete search history.

(56) References Cited

U.S. PATENT DOCUMENTS

| | | | | |
|---|---|---|---|---|
| 3,720,663 A | * | 3/1973 | Tessler .................... | C08B 31/06 536/106 |
| 4,020,272 A | * | 4/1977 | Tessler .................... | C08B 31/02 536/107 |
| 4,376,818 A | * | 3/1983 | Ohashi ................. | C07D 207/46 106/150.1 |
| 4,959,366 A | * | 9/1990 | Cross ................. | C07D 295/192 514/239.5 |
| 6,124,363 A | | 9/2000 | Appleby et al. | |

FOREIGN PATENT DOCUMENTS

| | | |
|---|---|---|
| CN | 1453267 | 5/2003 |
| IN | 201621006491 | 1/2017 |

OTHER PUBLICATIONS

Cross P. E., Arrowsmith J. E., Thomas G. N., Gwilt M., Burges R. A., Higgins A. J., J. Med. Chem., 1990, 33, 1151-1155.
Rosen B. R., Ruble J. C., Beauchamp T. J., Navarro A., *Org. Lett.*, 2011, 13, 2564-2567, Abstract.
CZ Search Report regarding Application No. PV 2017-772, Aug. 27, 2018.

\* cited by examiner

*Primary Examiner* — Amy C Bonaparte
(74) *Attorney, Agent, or Firm* — Pearl Cohen Zedek Latzer Baratz LLP

(57) ABSTRACT

A method for preparing 1-(4-methanesulfonamidophenoxy)-2-[N-(4-methanesulfonamidophenethyl)-N-methylamino] ethane (Dofetilide) of formula I by sulfonylation of 1-(4-aminophenoxy)-2-[N-(4-aminophenethyl)-N-methylamino] ethane of formula II with N-methylsulfonyl-N'-methylimidazolium chloride of formula III.

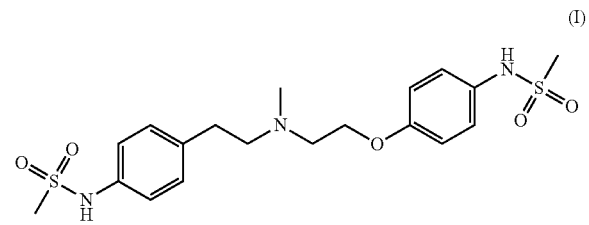

(I)

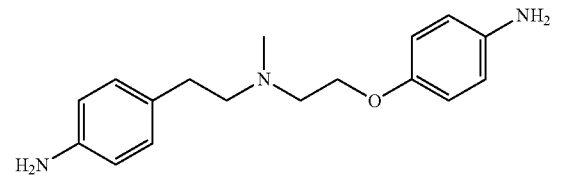

(II)

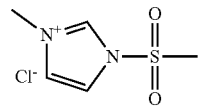

(III)

4 Claims, No Drawings

METHOD FOR PREPARING N-[4-(2-{[2-(4-METHANE SULFONAMIDOPHENOXY) ETHYL] (METHYL)AMINO}ETHYL)PHENYL] METHANESULFONAMIDE (DOFETILIDE)

CROSS-REFERENCE TO RELATED APPLICATIONS

This application is claiming the benefit of Czech Patent Application No. CZ 2017-772, filed Dec. 1, 2017 which is hereby incorporated by reference.

TECHNICAL FIELD

The invention relates to a new preparation method of 1-(4-methanesulfonamidophenoxy)-2-[N-(4-methanesulfonamidophenethyl)-N-methylamino]ethane (Dofetilide), the compound of formula I.

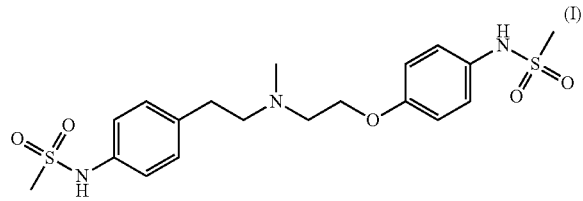 [SMILES: CN(CCOc1ccc(NS(C)(=O)=O)cc1)CCc1ccc(NS(C)(=O)=O)cc1]

1-(4-methanesulfonamidophenoxy)-2-[N-(4-methanesulfonamidophenethyl)-N-methylamino]ethane (Dofetilide) belongs to class III antiarrhytmics.

BACKGROUND ART 1-(4-methanesulfonamidophenoxy)-2-[N-(4-methanesulfonamidophenethyl)-N-methylamino]ethane (Dofetilide) is prepared by sulfonylation of 1-(4-aminophenoxy)-2-[N-(4-aminophenethyl)-N-methylamino]ethane, the compound of formula II.

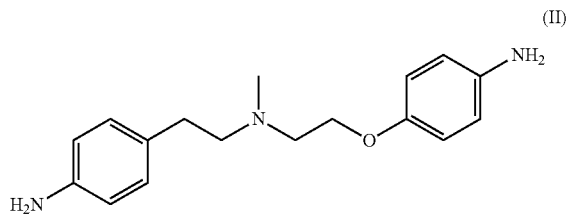 [SMILES: CN(CCOc1ccc(N)cc1)CCc1ccc(N)cc1]

Preparation of 1-(4-methanesulfonamidophenoxy)-2-[N-(4-methanesulfonamidophenethyl)-N-methylamino]ethane (Dofetilide) was first described in EP0245997 through a reaction of 1-(4-aminophenoxy)-2-[N-(4-aminophenethyl)-N-methylamino]ethane with the anhydride of methanesulfonic acid (methanesulfonic anhydride). The starting compound reacts with methanesulfonic anhydride in a dichloromethane environment without the use of a base. Disadvantages of this procedure include the price of methanesulfonic anhydride and at the same time an inconvenient atom economy of the process. The same procedure was subsequently described in the reference literature (Cross P. E., Arrowsmith J. E., Thomas G. N., Gwilt M., Burges R. A., Higgins A. J., *J. Med. Chem.*, 1990, 33, 1151-1155). Preparation of 1-(4-methanesulfonamidophenoxy)-2-[N-(4-methanesulfonamidophenethyl)-N-methylamino]ethane (Dofetilide) was further described in U.S. Pat. No. 6,124,363, where methanesulfonyl chloride is used as the sulfonylation agent in the presence of triethylamine. Methanesulfonyl chloride is a very reactive agent and under the described conditions, undesired methanesulfonimides are produced, which must be hydrolyzed with use of sodium hydroxide during the processing of the reaction mixture. Subsequently, the product is isolated by adjustment of pH of the mixture and filtration. The product is separated in the form of a fine precipitate, the filtration of which is time consuming. In addition, the product may be polluted by inorganic salts. 1-(4-Methanesulfonamidophenoxy)-2-[N-(4-methanesulfonamidophenethyl)-N-methylamino]ethane (Dofetilide) has also been synthesized by arylation of methanesulfonamide catalyzed by palladium (Rosen B. R., Ruble J. C., Beauchamp T. J., Navarro A., *Org. Lett.*, 2011, 13, 2564-2567); this method has drawbacks in the price of the used catalyst and ligand and contamination of the product by palladium.

The said disadvantages are eliminated by the method according to the invention.

DISCLOSURE OF THE INVENTION

The invention provides a method for preparing 1-(4-methanesulfonamidophenoxy)-2-[N-(4-methanesulfonamidophenethyl)-N-methylamino]ethane (Dofetilide) of formula I by reaction of 1-(4-aminophenoxy)-2-[N-(4-aminophenethyl)-N-methylamino]ethane with N-methylsulfonyl-N'-methylimidazolium chloride of formula III.

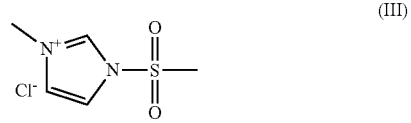

The reaction runs with complete conversion without the occurrence of a significant quantity of undesired methanesulfonimides. N-Methylsulfonyl-N'-methylimidazolium chloride is preferably prepared in situ by reaction of 1-methylimidazole with methanesulfonyl chloride. 1-Methylimidazole is preferably used in excess. The sulfonylation product is isolated by extraction into ethyl acetate, from which Dofetilide crystallizes after concentration and addition of a suitable antisolvent.

The substance of the invention comprises (A) preparing a solution of N-methylsulfonyl-N'-methylimidazolium chloride in an inert solvent by reaction of 1-methylimidazole with methanesulfonyl chloride.

(B) reacting N-methylsulfonyl-N'-methylimidazolium chloride with 1-(4-aminophenoxy)-2-[N-(4-aminophenethyl)-N-methylamino]ethane of formula II to produce 1-(4-methanesulfonamidophenoxy)-2-[N-(4-methanesulfonamidophenethyl)-N-methylamino]ethane of formula I.

Preferably, the preparation of N-methylsulfonyl-N'-methylimidazolium chloride in step (A) is carried out by reaction of methanesulfonyl chloride with an excess of 1-methylimidazole. 1-Methylimidazole is preferably used in a quantity of 1.05 to 2 mol, more preferably 1.08 mol per 1 mol of methanesulfonyl chloride.

Another preferred embodiment of the invention consists in that the preparation of N-methylsulfonyl-N'-methylimidazolium chloride in step (A) is carried out in an inert solvent at a temperature of −20 to 25° C., preferably at −15 to −5° C.

N-Methylpyrrolidone, N,N-dimethylformamide and N,N-dimethylacetamide or their mixtures can be used as the inert solvents in step A.

Another preferred embodiment of the invention consists in that the preparation of 1-(4-methanesulfonamidophenoxy)-2-[N-(4-methanesulfonamidophenethyl)-N-methylamino]ethane in step B is carried out by addition of a solution of 1-(4-aminophenoxy)-2-[N-(4-aminophenethyl)-N-methylamino]ethane in an inert solvent to the solution of N-methylsulfonyl-N'-methylimidazolium chloride prepared in step A at a temperature of −20 to 25° C., preferably at −15 to −5° C.

N-Methylpyrrolidone, N,N-dimethylformamide and N,N-dimethylacetamide or their mixtures can be used as the inert solvents in step B.

The produced 1-(4-methanesulfonamidophenoxy)-2-[N-(4-methanesulfonamidophenethyl)-N-methylamino]ethane (Dofetilide) is, after stopping of the reaction by addition of an aqueous solution of sodium sulphite and sodium hydrogen carbonate, extracted with ethyl acetate, from which it crystallizes after concentration.

The crystalline suspension is subsequently heated up to boil to produce a well-filterable crystalline form of the product.

Then, cyclohexane is added to the crystalline suspension to complete precipitation of the product, the separated Dofetilide is isolated, washed with a mixture of ethyl acetate with cyclohexane and dried.

The main advantage of the inventive method is that it does not produce undesired sulfonimides, i.e. there is no need to carry out their hydrolysis.

EXAMPLES

The substance of the inventive method is clarified in a more detailed way in the examples below. These examples have an illustrative character and do not restrict the scope of the invention in any respect.

Example 1

1-Methylimidazole (46.6 g, 568 mmol) and subsequently N-methylpyrrolidone (255 ml) are charged into a sulfonation flask fitted with a thermometer, mechanical stirrer and a dropping funnel. The obtained solution is cooled down to −15° C. under a nitrogen atmosphere. During 20 min, methanesulfonyl chloride (60.2 g, 526 mmol) is added dropwise, the temperature of the reaction mixture is maintained in the range of −15 to −7° C. The dropping funnel is rinsed with N-methylpyrrolidone (28 ml). The addition being completed, the mixture is stirred for 5 min at about −10° C. and subsequently a solution of 1-(4-aminophenoxy)-2-[N-(4-aminophenethyl)-N-methylamino]ethane (60.0 g, 210 mmol) in N-methylpyrrolidone (240 ml) is added dropwise during 20 min. The dropping funnel is rinsed with N-methylpyrrolidone (20 ml). During the addition, the temperature is maintained in the range of −12 to −5° C. Then, the reaction mixture is maintained at about −15 to −10° C. for 30 min. After this time period, HPLC conversion is >99.9%. The reaction is stopped by addition of 15.8 g of a 10% aqueous solution of $Na_2SO_3$. The reaction mixture is left to get heated up to about 0° C. A solution of $NaHCO_3$ (56.4 g) in water (600 ml) is added dropwise to the reaction mixture. The mixture is extracted with ethyl acetate (6×600 ml). The combined organic phases are then washed with a 10% aqueous solution of NaCl (6×600 ml). About 9/10 of the solvent volume is removed by distillation at reduced pressure; the final volume should correspond to about 300 ml. During the distillation, crystals start to get separated. Subsequently, the mixture is heated up to boil at atmospheric pressure and stirred under boiling for 1 h. The mixture is cooled down to the room temperature and cyclohexane (300 ml) is added to the obtained suspension during 5 min. The mixture is stirred at room temperature for 1 h. The separated crystals are filtered off and washed with a mixture of ethyl acetate (120 ml) and cyclohexane (120 ml). The product is dried and 83.1 g (90%) of a creamy crystalline substance is obtained. HPLC purity 99.8%. HRMS (ESI+) m/z calculated for $[C_{19}H_{27}O_5N_3S_2+H]^+$: 442.1465; found: 442.1461.

Example 2

A solution of 1-methylimidazole (2.33 g, 28.4 mmol) in N,N-dimethylformamide (13 ml) is cooled down to −15° C. Methanesulfonyl chloride (3.01 g, 26.3 mmol) is added to the solution dropwise; the temperature is maintained in the range of −18 to −15° C. The mixture is subsequently stirred at this temperature for 5 min. A solution of 1-(4-aminophenoxy)-2-[N-(4-aminophenethyl)-N-methylamino]ethane (3.0 g, 10.5 mmol) in N,N-dimethylformamide (12 ml) is then added dropwise to the reaction mixture during 20 min. During the addition, the temperature is maintained in the range of −20 to −13° C. The dropping funnel is rinsed with N,N-dimethylformamide (1 ml). The reaction mixture is stirred at −15° C. for 30 min. After this time period, HPLC conversion is >99.9%. A 10% aqueous solution of $Na_2SO_3$ (0.8 ml) is added to the reaction mixture and the reaction mixture is left to heat up to about 0° C. Subsequently, a solution of $NaHCO_3$ (2.82 g) in water (30 ml) is added dropwise. The mixture is extracted with ethyl acetate (6×30 ml). The combined extracts are then washed with a 10% aqueous solution of NaCl (6×30 ml). The organic phase is concentrated to a volume of about 15 ml. The obtained suspension is heated up to boil for 1 h and then it is cooled down to the room temperature. Cyclohexane (15 ml) is added to the mixture under stirring. The crystalline substance is filtered off and washed with a cooled mixture of ethyl acetate (6 ml) and cyclohexane (6 ml). The product is dried and 3.73 g (80%) of a creamy crystalline substance is obtained. HPLC purity 99.5%. HRMS (ESI+) m/z calculated for $[C_{19}H_{27}O_5N_3S_2+H]^+$: 442.1465; found: 442.1461.

Example 3

A solution of 1-methylimidazole (2.33 g, 28.4 mmol) in N,N-dimethylacetamide (13 ml) is cooled down to −18° C. Methanesulfonyl chloride (3.01 g, 26.3 mmol) is added to the solution dropwise; the temperature is maintained in the range of −18 to −15° C. The mixture is stirred at this temperature for 5 minutes. A solution of 1-(4-aminophenoxy)-2-[N-(4-aminophenethyl)-N-methylamino]ethane (3.0 g, 10.5 mmol) in N,N-dimethylacetamide (12 ml) is subsequently added to the reaction mixture dropwise during 20 min. During the addition, the temperature is maintained in the range of −18 to −12° C. The dropping funnel is rinsed with N,N-dimethylacetamide (1 ml). The reaction mixture is stirred at −15° C. for 30 min. After this time period, HPLC conversion is >99.9%. A 10% aqueous solution of $Na_2SO_3$ (0.8 ml) is added to the reaction mixture and the reaction mixture is left to heat up to about 0° C. Subsequently, a solution of NaHCO₃ (2.82 g) in water (30 ml) is added dropwise. The mixture is extracted with ethyl acetate (6×30 ml). The combined extracts are then washed with a 10% aqueous solution of NaCl (6×30 ml). The organic phase is concentrated to a volume of about 15 ml. The obtained suspension is heated up to boil for 1 h and then it is cooled down to the room temperature. Cyclohexane (15 ml) is added to the mixture under stirring. The crystalline substance is filtered off and washed with a cooled mixture of ethyl acetate (6 ml) and cyclohexane (6 ml). The product is dried and 3.59 g (77%) of a creamy crystalline substance is obtained. HPLC purity 99.5%. HRMS (ESI+) m/z calculated for $[C_{19}H_{27}O_5N_3S_2+H]^+$: 442.1465; found: 442.1459.

The invention claimed is:

1. A method for preparing 1-(4-methanesulfonamidophenoxy)-2-[N-(4-methane-sulfonamidophenethyl)-N-methylamino]ethane (Dofetilide) of formula I

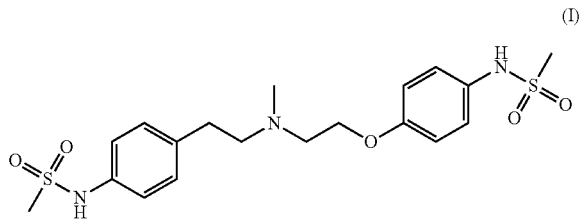 [SMILES: CN(CCOc1ccc(NS(C)(=O)=O)cc1)CCc1ccc(NS(C)(=O)=O)cc1]

by sulfonylation of 1-(4-aminophenoxy)-2-[N-(4-aminophenethyl)-N-methylamino]ethane of formula II,

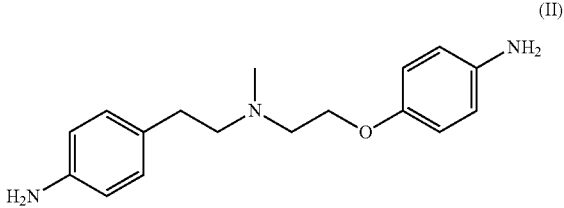 [SMILES: CN(CCOc1ccc(N)cc1)CCc1ccc(N)cc1]

characterized in that the sulfonylation is carried out with N-methylsulfonyl-N'-methylimidazolium chloride of formula III

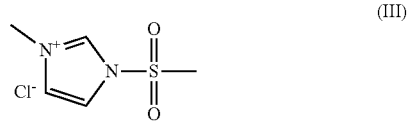

in an organic solvent.

2. The method according to claim 1, characterized in that N-methylsulfonyl-N'-methylimidazolium chloride prepared by reaction of 1-methylimidazole with methanesulfonyl chloride is used.

3. The method according to claim 1, characterized in that the organic solvent is N-methylpyrrolidone, N,N-dimethylformamide, N,N-dimethylacetamide or their mixture.

4. The method according to claim 1, characterized in that the reaction is carried out at a temperature of −20 to −5° C.

* * * * *